United States Patent
Teshima et al.

(10) Patent No.: US 10,128,015 B2
(45) Date of Patent: Nov. 13, 2018

(54) X-RAY SHIELD GRATING AND X-RAY TALBOT INTERFEROMETER INCLUDING X-RAY SHIELD GRATING

(71) Applicant: CANON KABUSHIKI KAISHA, Tokyo (JP)

(72) Inventors: Takayuki Teshima, Yokohama (JP); Takashi Nakamura, Yokohama (JP); Genta Sato, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/698,735

(22) Filed: Apr. 28, 2015

(65) Prior Publication Data
US 2015/0316494 A1 Nov. 5, 2015

(30) Foreign Application Priority Data

Apr. 30, 2014 (JP) .................................. 2014-093889
Jan. 15, 2015 (JP) .................................. 2015-005924

(51) Int. Cl.
*G21K 1/06* (2006.01)
*G01N 23/20* (2018.01)
*A61B 6/00* (2006.01)

(52) U.S. Cl.
CPC ............. *G21K 1/06* (2013.01); *A61B 6/4035* (2013.01); *G21K 1/067* (2013.01); *A61B 6/484* (2013.01); *G01N 23/20075* (2013.01); *G21K 2201/064* (2013.01); *G21K 2201/067* (2013.01)

(58) Field of Classification Search
CPC ............. G21K 1/067; G21K 2201/064; G21K 2201/067; A61B 6/484; G01N 23/20075
See application file for complete search history.

(56) References Cited

U.S. PATENT DOCUMENTS

| | | | |
|---|---|---|---|
| 2007/0183582 A1* | 8/2007 | Baumann | A61B 6/484 378/145 |
| 2012/0002785 A1* | 1/2012 | Kaneko | G21K 1/067 378/62 |
| 2012/0288056 A1* | 11/2012 | Murakoshi | A61B 6/4233 378/37 |
| 2016/0265125 A1* | 9/2016 | Yokoyama | C25D 1/00 |

FOREIGN PATENT DOCUMENTS

| | | |
|---|---|---|
| JP | 2007206075 A | 8/2007 |
| JP | 201213530 A | 1/2012 |

* cited by examiner

*Primary Examiner* — Eliza Osenbaugh-Stewart
(74) *Attorney, Agent, or Firm* — Canon USA, Inc., IP Division

(57) ABSTRACT

An X-ray shield grating includes a substrate on which a plurality of recessed portions are arranged, and metal that is arranged in each of the recessed portions. The substrate includes a bent region that is bent in an arrangement direction in which the plurality of recessed portions are arranged. A radius of curvature of the bent region is 200 millimeters or less. In the bent region, a maximum value of a width of a region sandwiched between two adjacent recessed portions of the plurality of recessed portions and a width of the substrate in an end portion of the bent region are less than or equal to three times a minimum value of the width of the region sandwiched between the two adjacent recessed portions.

9 Claims, 10 Drawing Sheets

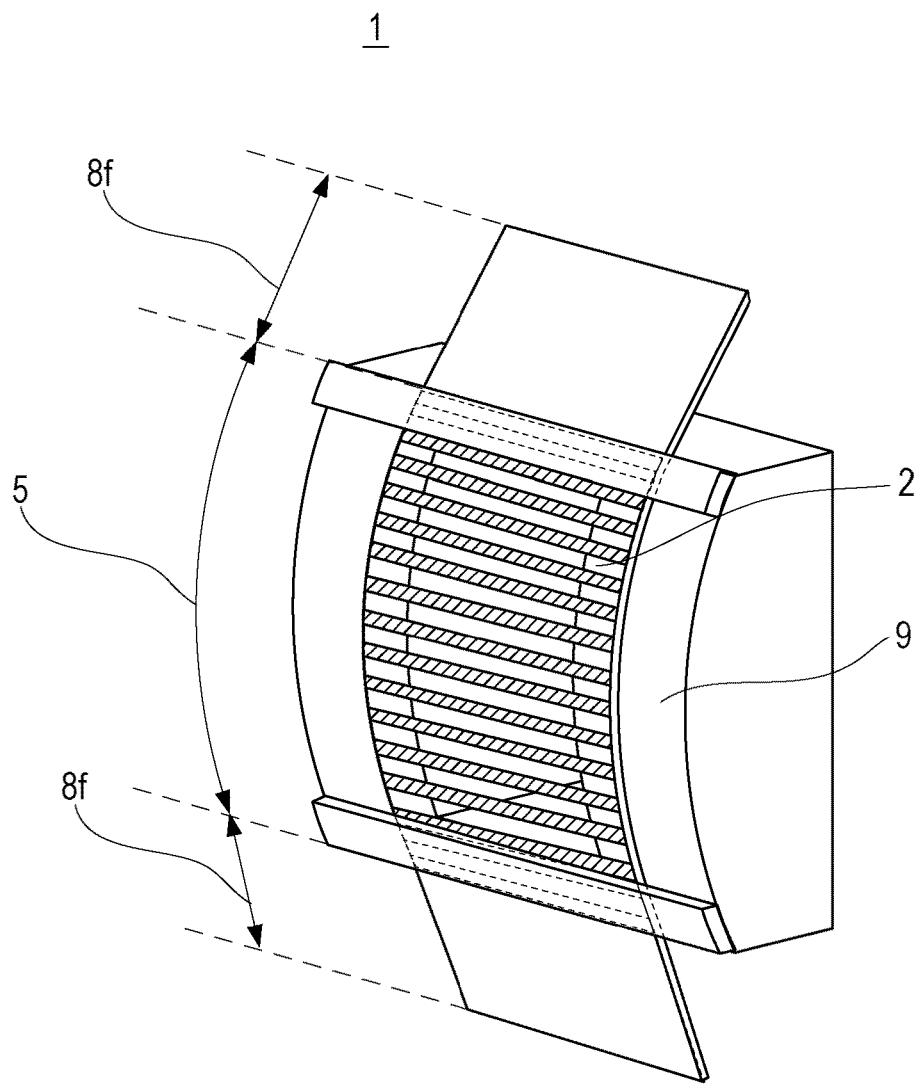

X-RAY SHIELD GRATING AND X-RAY TALBOT INTERFEROMETER INCLUDING X-RAY SHIELD GRATING

BACKGROUND

Field of the Invention

The present disclosure relates to an X-ray shield grating and an X-ray Talbot interferometer including the X-ray shield grating.

Description of the Related Art

Gratings including a structural body having a periodic structure have been used as optical elements for various apparatuses. In particular, gratings formed of metal with a high X-ray absorptivity have been used as X-ray shield gratings for non-destructive tests for objects and in the area of medical care.

As a use application of X-ray shield gratings, shield gratings in X-ray Talbot interferometers have been known. An imaging method using an X-ray Talbot interferometer (X-ray Talbot interference method) is one of methods for acquiring information of a subject by using a phase change of an X ray by the subject.

An X-ray Talbot interference method will be briefly explained below. In an X-ray Talbot interferometer, spatially coherent X rays pass through a diffraction grating which diffracts X rays and through a subject, and forms an interference pattern. At a position where the interference pattern is formed, a shield grating for periodically shielding X rays is arranged to form moire. The moire is detected by a detector, and information of the subject can be obtained from the detection result.

General X-ray shield gratings used in the X-ray Talbot interference method have a structure in which X-ray transmission portions and X-ray shielding portions are arranged periodically. The X-ray shielding portions often include a high-aspect-ratio structural body (the aspect ratio represents the ratio of height or depth h to width w (h/w) of a structural body) formed of metal with a high X-ray absorptivity, such as gold.

Furthermore, a shield grating having such a structure may be used not to form moire by partially shielding X rays which form the interference pattern as described above but to improve the spatial coherency of X rays. The shield grating used as described above is called a source grating (or a light source grating). A shield grating arranged at a position where an interference pattern is formed may be called an analysis grating. Both the source grating used to improve the coherency of X rays and the analysis grating used to form moire are X-ray shield gratings. Therefore, hereinafter, these gratings will be called a source grating and an analysis grating when it is necessary to distinguish between them, and they will be collectively called X-ray shield gratings when both the gratings are referred to. Furthermore, hereinafter, simple expressions, such as a transmission portion, a shielding portion, and a shield grating, represent an X-ray transmission portion, an X-ray shielding portion, and an X-ray shield grating, respectively.

When a source grating is arranged between an X-ray source and a diffraction grating, a state in which microfocus X-ray sources are virtually arranged can be generated. An X-ray source with a smaller focal point (X-ray generation part) has a higher spatial coherency of X rays generated from the X-ray source. Therefore, the use of such a source grating improves the spatial coherency of X rays. A Talbot interference method, which is a type of Talbot interference method implemented by generating the state in which microfocus X-ray sources are virtually arranged, may be called a Talbot-Lau interference method, in order to distinguish it from a Talbot interference method using no source grating.

Planar shield gratings are effective for the case where a Talbot interference method is used with parallel light (parallel X rays), which is used in a synchrotron radiation facility. However, in a Talbot interference method using an X-ray source which emits divergent light (divergent X rays), such as an X-ray tube used in a laboratory, a deviation between the traveling direction of X rays and the height direction of shielding portions increases as the distance from the optical axis (X-ray axis) increases, and so-called vignetting occurs. Thus, X rays which are desired to transmit through a shield grating are also shielded. Therefore, an insufficient X-ray transmission contrast is obtained, and the amount of X rays which reach a detector decreases. Accordingly, the contrast of X-ray intensity distribution detected by the detector decreases in a region distant from the optical axis.

Japanese Patent Laid-Open No. 2007-206075 discloses a method for making the traveling direction of X rays and the height direction of shielding portions the same by bending at least one of a source grating, a diffraction grating, and an analysis grating used for a Talbot interferometer.

SUMMARY

An X-ray shield grating as disclosed herein includes a substrate on which a plurality of recessed portions are arranged, and metal that is arranged in each of the recessed portions. The substrate includes a bent region that is bent in an arrangement direction in which the plurality of recessed portions are arranged. A radius of curvature of the bent region is 200 millimeters or less. In the bent region, in a case where a maximum value of a width of a region sandwiched between two adjacent recessed portions of the plurality of recessed portions is less than or equal to three times a minimum value of the width of the region sandwiched between the two adjacent recessed portions, and in a case where a width of the substrate in an end portion of the bent region represents a shortest distance from the end portion to the metal when the end portion is part of the substrate, and represents 0 when the end portion is part of the metal, the width of the substrate in the end portion of the bent region being less than or equal to three times the minimum value.

Further features of the present invention will become apparent from the following description of exemplary embodiments with reference to the attached drawings.

BRIEF DESCRIPTION OF THE DRAWINGS

FIG. 7 is a diagram for explaining a method for producing an X-ray shield grating according to Example 3 discussed herein.

DESCRIPTION OF THE EMBODIMENTS

Figure 1A:
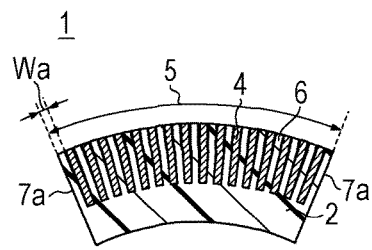
FIGS. 1A to 1G are cross-sectional views according to an embodiment of the present disclosure.

As described above, Japanese Patent Laid-Open No. 2007-206075 discloses a method for making the traveling direction of X rays and the height direction of a shielding portion the same by bending at least one of a source grating, a diffraction grating, and an analysis grating used for a Talbot interferometer. However, inventors of the present invention have found a problem that when force is externally applied to a shield grating with a certain radius of curvature so that the shield grating is bent, the bending stress applied to the shield grating may exceed its breaking stress and the shield grating may therefore be broken.

In an embodiment of the present invention, an X-ray shield grating which is a bent shield grating and has a structure less susceptible to breakage when being produced, and an X-ray Talbot interferometer which includes the X-ray shield grating will be explained. An X-ray shield grating according to an embodiment includes a substrate on which a plurality of recessed portions are arranged, and metal which is arranged in each of the recessed portions. In the X-ray shield grating, the plurality of recessed portions are arranged when viewed from an X-ray source side (that is, so that the height direction of the recessed portions and the traveling direction of X rays are substantially the same). The metal arranged in each of the recessed portions function as a shielding portion, and a portion sandwiched between two adjacent recessed portions (hereinafter, may be referred to as a protruding portion) and a portion sandwiched between an end face of the substrate and a recessed portion function as transmission portions.

Furthermore, the X-ray shield grating has a bent region which is bent in the direction in which the plurality of recessed portions are arranged. The radius of curvature of this bent region is 200 millimeters or less. The radius of curvature of a bent region represents the radius of curvature of a substrate surface on the outer side of the bending on the cross section obtained by cutting out the bent region in the direction in which the plurality of recessed portions are arranged.

In a bent region of an X-ray shield grating according to an embodiment, the maximum value of the width of protruding portions is less than or equal to three times the minimum value of the width of the protruding portions. With a protruding portion having a large width, the bending stress is easily concentrated on a portion between the protruding portion and a recessed portion that is in contact with the protruding portion. A discussion by the inventors of the present invention has found that in the case where, in particular, the radius of curvature of a bent region is 200 millimeters or less when a silicon substrate or a glass substrate is used as a substrate, such a concentration of the bending stress tends to easily cause breakage of the substrate. In addition to this, a further discussion by the inventors has found that in the case where the maximum value of the width of the protruding portions in the bent region is set to be less than or equal to three times the minimum value of the width of the protruding portions, even if the radius of curvature of the bent region is 200 millimeters or less, the substrate is less susceptible to breakage. This is considered to be because when the maximum value of the width of the protruding portions in the bent region is less than or equal to three times the minimum value of the width of the protruding portions, local concentration of the bending stress is suppressed and the bending stress is distributed between each of protruding portions and each of recessed portions throughout the bent region.

Figure 9:
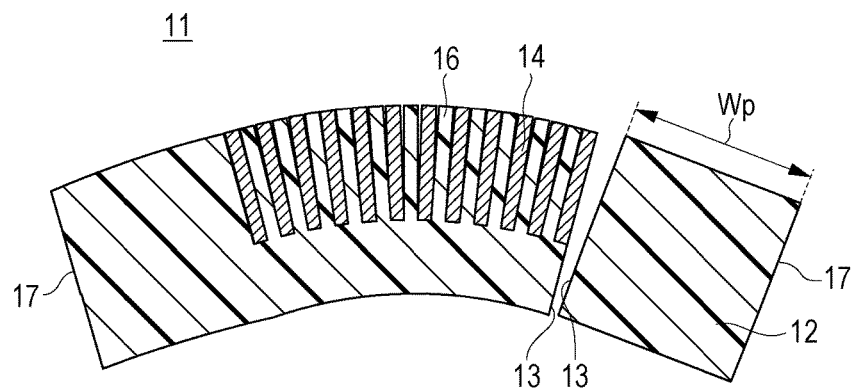
FIG. 9 is a diagram according to a comparative example.

FIG. 9 illustrates an X-ray shield grating 11 according to a comparative example. In the X-ray shield grating 11 illustrated in FIG. 9, a recessed portion is not formed at an end of a substrate 12, and the width Wp of the substrate in an end portion 17 of the substrate 12 is more than three times the minimum value of the width of other protruding portions 16. Furthermore, metal 14 is arranged in each of the recessed portions. When the X-ray shield grating 11 with this configuration is bent, the bending stress is concentrated on a portion 13, which is between a region of the substrate from the end portion 17 to the recessed portion closest to the end portion 17 and the recessed portion closest to the end portion 17. When the radius of curvature is 200 millimeters or less, the substrate 12 is easily broken by the bending stress.

In an X-ray shield grating according to an embodiment, the width of a substrate in an end portion of a bent region is also less than or equal to three times the minimum value of the width of protruding portions in the bent region. Therefore, concentration of the bending stress on a portion between the end portion of the substrate and the recessed portion closest to the end portion can be suppressed, and the substrate becomes less susceptible to breakage even if the radius of curvature of the bent region is 200 millimeters or less. When the end portion does not include part of metal arranged in the recessed portions, the width of the substrate in the end portion of the bent region represents the shortest distance from the end portion to the metal (that is, an X-ray shielding portion). When the end portion includes part of the metal arranged in the recessed portions, the width of the substrate in the end portion represents 0. Furthermore, the end portion of the bent region represents an end face of the bent region. However, if only part of the substrate is a bent region, by assuming a virtual end face of the bent region, the assumed virtual face is regarded as an end portion of the bent region.

Hereinafter, embodiments of the present invention will be described more specifically with reference to drawings.

FIGS. 1A to 1G and FIG. 2 are schematic diagrams of an X-ray shield grating 1 according to an embodiment of the present invention.

The X-ray shield grating 1 according to this embodiment includes a substrate 2 on which a plurality of recessed portions are arranged, and metal 4 which is arranged in each of the recessed portions.

A silicon substrate or a glass substrate may be used as the substrate 2. The glass substrate represents a substrate made of quartz, non-lead glass, or soda lime glass. Silicon is a material capable of forming a recessed portion with a high verticality by etching with a strong alkaline aqueous solution which utilizes a crystallographic orientation plane. Furthermore, silicon is suitable for forming a recessed portion with a high aspect ratio by a Bosch process in which etching using $SF_6$ gas for reactive ion etching (RIE) and deposition of side wall protection films by $C_4F_8$ gas are alternatively performed. Therefore, preferably, a silicon substrate is used as the substrate 2. The substrate 2 preferably has a smaller thickness because the X-ray transmission rate in the X-ray transmission portions increases as the thickness of the substrate 2 decreases. Specifically, preferably, the thickness of the substrate 2 is 500 micrometers or less, and more preferably, 300 micrometers or less. However, it is difficult to handle a too-thin substrate during processing, and therefore the thickness is selected appropriately. Furthermore, in the case where a silicon substrate is used, it is preferable that the angle formed by the direction in which a plurality of recessed portions are arranged and a crystal axis <110> of the silicon substrate is equal to or more than 1 degree and less than or equal to 45 degrees, and more preferably, equal to or more than 30 degrees and less than or equal to 45 degrees. Furthermore, it is also preferable that the angle formed by a bent direction and the crystal axis <110> of the silicon substrate is equal to or more than 1 degree and less than or equal to 45 degrees, and more preferably, equal to or more than 30 degrees and less than or equal to 45 degrees.

This is because bending parallel to the direction of the crystal axis <110> of the silicon substrate easily causes cleavage and thus setting the angle formed by the direction in which the plurality of recessed portions are arranged and the crystal axis <110> of the silicon substrate to fall within the above range reduces the possibility of breakage of the silicon substrate caused by the cleavage.

Figure 2:
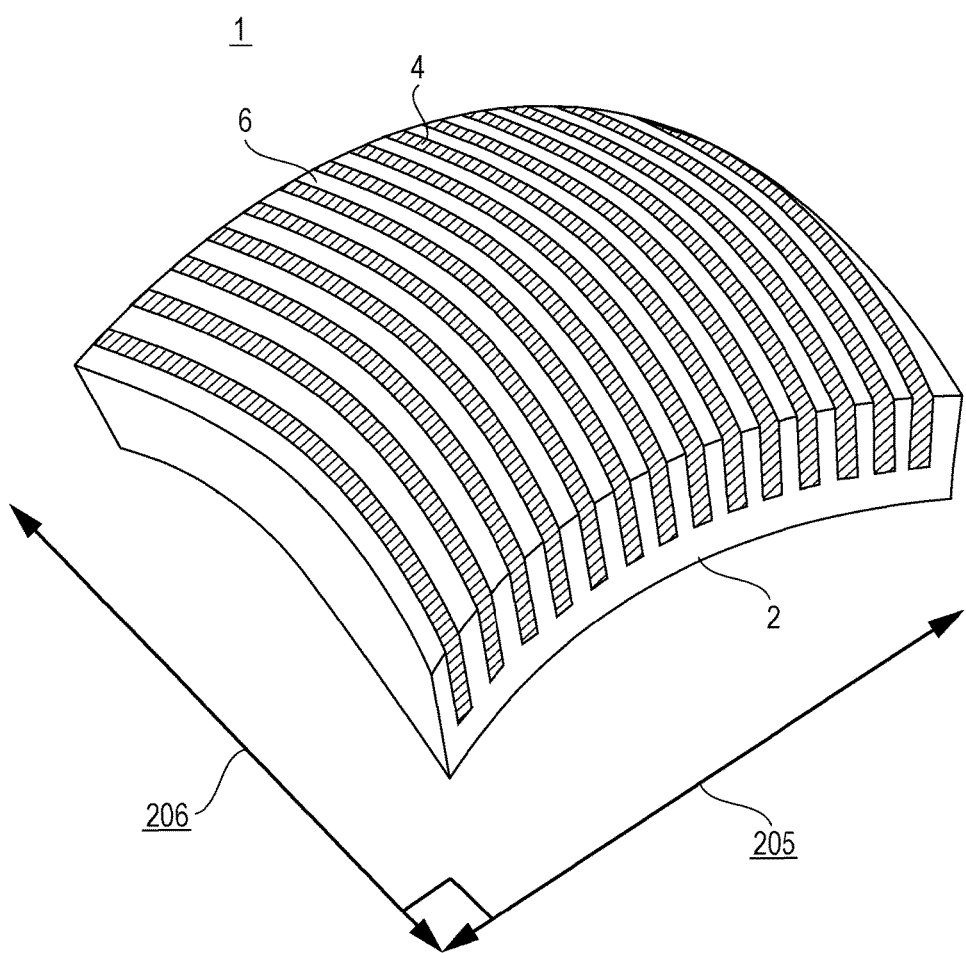
FIG. 2 is a perspective view for explaining an embodiment of the present disclosure.

As illustrated in the perspective view of FIG. 2, it is preferable that the cross section obtained by cutting the plurality of recessed portions in the direction perpendicular to the height direction has a line shape. Hereinafter, such recessed portions may be simply referred to as line-shaped recessed portions. In the case where each of the plurality of recessed portions has a line shape, the X-ray shield grating 1 includes line-shaped shielding portions and line-shaped transmission portions each of which is sandwiched between two shielding portions. Such a pattern of the shield grating is called a line-and-space pattern. Even if the line-shaped recessed portions are connected through end portions thereof, when the recessed portions are not connected to each other in a grating region, the recessed portions are regarded as being independent of each other, and a region sandwiched between the recessed portions is regarded as a region sandwiched between two adjacent recessed portions. The grating region may be set appropriately.

The cross section of the recessed portions illustrated in each of FIGS. 1A to 1G and FIG. 2 is rectangular, and the recessed portions are formed perpendicular to the substrate. However, the cross section of the recessed portions may have a forward-tapered shape or a reverse-tapered shape. Furthermore, the recessed portions illustrated in FIGS. 1A to 1G and FIG. 2 have a constant width (length in the arranged direction) and space. However, neither the width nor the space of the recessed portions needs to be constant in a bent region.

The metal 4 may be metal with a high X-ray shield factor. For example, gold, copper, iron, nickel, tin, palladium, platinum, or an alloy of the above metal may be used as the metal 4. In particular, gold, which is a high X-ray shield factor and which is easily arranged in the recessed portions, or an alloy of gold may be preferably used.

The height of the metal 4 is not necessarily equal to the height of the recessed portions. That is, the metal 4 is not necessarily filled up to the top face of the recessed portions, and the metal 4 may overflow the recessed portions. However, if the amount of overflow from the recessed portions is large and metal is therefore arranged on the substrate that functions as the transmission portions, the X-ray transmission rate of the X-ray transmission portions decreases, which is not preferable. Therefore, it is preferable that the height of the metal is less than or equal to the height of the recessed portions.

Furthermore, in this embodiment, a region of the substrate that functions as the X-ray transmission portions may not be exposed. For example, a face of the substrate 2 on which an insulation film or the like is formed may be exposed, and a portion of the substrate that is sandwiched between recessed portions may function as an X-ray transmission portion.

The X-ray shield grating 1 includes a bent region 5. The bent region 5 is a region which is bent in the direction in which the plurality of recessed portions are arranged. The radius of curvature of the bent region is 200 millimeters or less. In the present invention and the description, a region which is bent in the direction in which the plurality of recessed portions are arranged but whose radius of curvature is more than 200 millimeters is not referred to as a bent region. In the case where the X-ray shield grating includes such a region, the region is regarded as an outer frame region. The outer frame region represents a region of the X-ray shield grating other than the bent region. A region other than the bent region is regarded as an outer frame region, irrespective of whether or not bending exists or whether or not a recessed portion is provided. Furthermore, the outer frame region is not limited to a region having a frame shape. In the case where a Talbot interference method is performed, it is preferable that part of or the entire bent region is used as a grating region, without using the outer frame region.

As described above, the radius of curvature of a bent region represents the radius of curvature of a substrate surface on the outer side of the bending on the cross section obtained by cutting the bent region in the direction in which the plurality of recessed portions are arranged. However, in the present invention and the description, the radius of curvature is obtained as described below.

Figure 3:
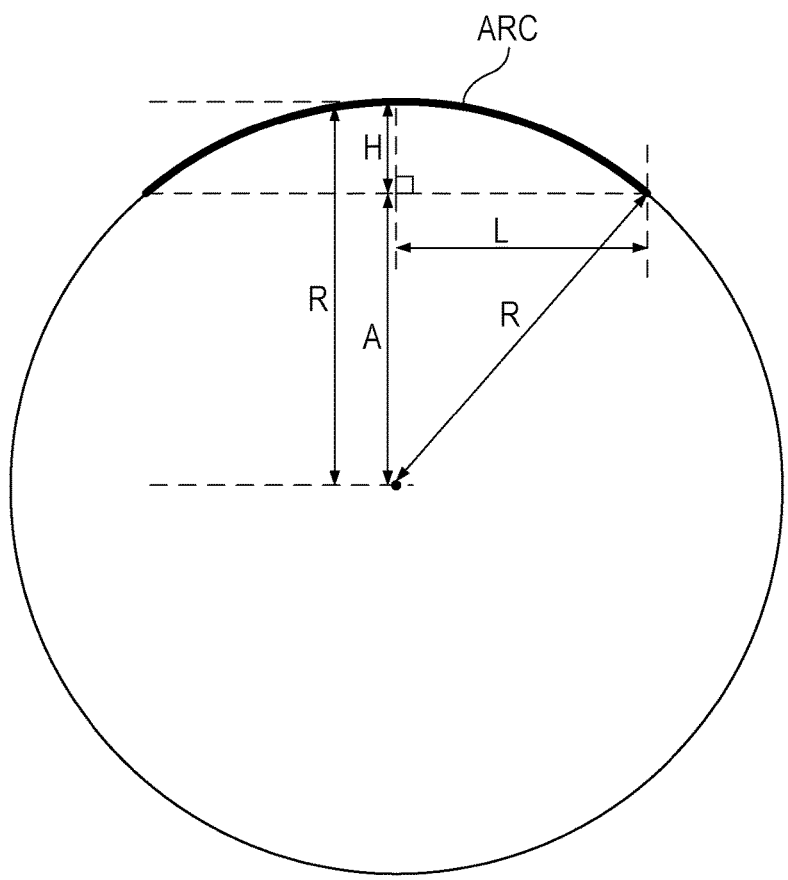
FIG. 3 is a diagram for explaining the definition of a radius of curvature.

A method for obtaining the radius of curvature in the present invention and the description will be explained with reference to FIG. 3. The radius R of curvature can be expressed by the equations below, where L represents a half of the width of an arc, and H represents the height of the arc.

$$R = A + H$$

$$R^2 = A^2 + L^2$$

By solving the two equations, the expression $R = (H + L^2/H)/2$ is obtained, and R, which is calculated using the expression, is defined as the radius of curvature in the present invention and the description.

In the case where the radius of curvature of the substrate is not constant, in order to locally obtain the radius of curvature, the arc is divided into short sections and the above method is performed for the divided arc. For example, in order to determine whether or not a shield grating which includes regions of different radiuses of curvature includes an outer frame region or to determine the position of the boundary between the outer frame region and the bent region, the arc along the bending of the shield grating may be divided into short sections to obtain the radius of curvature of each region.

In the cross section in the direction in which the plurality of recessed portions are arranged, the bent region may not be bent along the circumference of a perfect circle, and for example, the bent region may be bent along the circumference of an ellipse. That is, when it is assumed that the bent region is bent along part of a side face of a cylinder, the bottom face of the cylinder may be a perfect circle or an ellipse. As described above, even when the cross section of the bent region is not a perfect circle, the radius of curvature may be calculated using the above expression.

Furthermore, the bent region may also be bent in the direction perpendicular 206 to the direction in which the plurality of recessed portions are arranged 205. However, a deviation between the traveling direction of X rays in the direction perpendicular 206 to the direction in which the plurality of recessed portions are arranged 205 (corresponding to the direction in which the shielding portions of the X-ray shield grating are arranged) and the height direction of the shielding portions is less likely to cause vignetting of X rays compared to a deviation between the traveling direction of X rays in the direction in which the plurality of recessed portions are arranged and the height direction of the shielding portions. Therefore, the bent region is not necessarily bent in the direction perpendicular 206 to the direction in which the plurality of recessed portions are arranged 205. Even if the bent region is bent in the direction perpendicular 206 to the direction in which the plurality of recessed portions are arranged 205, the radius of curvature at the cross section obtained by cutting the bent region along the direction perpendicular 206 to the direction in which the plurality of recessed portions are arranged 205 may be more than 200 millimeters.

In the bent region of the X-ray shield grating according to this embodiment, the maximum value of the width of the protruding portions is less than or equal to three times the minimum value of the width of the protruding portions, and the width of the substrate in the end portion of the bent region is less than or equal to three times the minimum value of the width of the protruding portions. Due to a small difference of the width in a region of the substrate in the bent region where no recessed portion is formed, the bending stress may be distributed throughout the bent region, and concentration of the bending stress can thus be reduced. Therefore, the substrate in the bent region is less susceptible to breakage. If the width of a protruding portion is not constant, the width of a portion of a plurality of protruding portions with the largest width is defined as a maximum value of the protruding portions, and the width of a portion of the plurality of protruding portions with the smallest width is defined as a minimum value of the protruding portions. That is, the width of a protruding portion with the smallest width among a plurality of protruding portions may be defined as a minimum value of the width of the protruding portions, and the width of the protruding portion with the largest width among the plurality of protruding portions may be defined as a maximum value of the protruding portions.

In the case where a brittle material, such as silicon or glass, is used for the substrate 2, the material does not have a high malleability, unlike metal. Therefore, bending the substrate 2 on which recessed portions are formed easily causes breakage of the substrate, compared to the case where a substrate on which no recessed portion is formed is bent. This is because forming recessed portions on a substrate is substantially equal to forming flaws on the substrate and a portion where the flaws are formed is broken more easily than a portion where flaws are not formed. For example, in the X-ray shield grating 11 illustrated in FIG. 9, bending stress is easily concentrated on the portion 13 between the region of the substrate from the end portion of the bent region to the recessed portion closest to the end portion and the recessed portion closest to end portion, and the portion 13 is easily broken. Therefore, a portion of the substrate near the recessed portion closest to the end portion is easily broken.

In contrast, according to this embodiment, by setting the maximum value of the width of the protruding portions in the bent region and the width of the substrate in the end portion of the bent region to be less than or equal to three times the minimum value of the width of the protruding portions in the bent region, concentration of bending stress within the bent region can be distributed. Accordingly, the X-ray shield grating according to this embodiment has a structure which is less likely to cause breakage of the substrate.

A method for producing an X-ray shield grating according to an embodiment includes a step of cutting off at least an end portion of a substrate on which a plurality of recessed portions are arranged and metal is arranged in each of the recessed portions, and a step of bending the substrate whose end portion has been cut off, in an arrangement direction in which the plurality of recessed portions are arranged. In the bending step, a bent region is formed by bending the substrate. That is, in the bending step, the substrate whose end portion has been cut off is bent in such a manner that the radius of curvature of at least part of the substrate whose end portion has been cut off is 200 millimeters or less. Furthermore, in the step of cutting off the end portion, a region including the end portion is cut off in such a manner that the width of the substrate in the end portion of the bent region is less than or equal to three times the minimum value of the width of transmission portions in the bent region. In addition, it is preferable that the plurality of recessed portions formed in the region which is made to serve as the bent region by bending in the bending step performed later, of the substrate whose end portion is cut off in the step of cutting off the end portion, are formed in such a manner that the maximum value of the width of protruding portions is less than or equal to three times the minimum value of the width of the protruding portions. In other words, in the bending step, a region in which the maximum value of the width of the protruding portions and the width of the substrate in the end portion are less than or equal to three times the minimum value of the width of the protruding portions is bent in such a manner that the radius of curvature is less than equal to 200 millimeters. In the case where the substrate whose end portion has been cut off includes a region in which the maximum value of the width of the protruding portions is more than three times the minimum value of the width of the protruding portions, the region may be bent in such a manner that the radius of curvature is more than 200 millimeters or the region may not be bent. At this time, it is preferable that the width of the substrate in the end portion of the bent region is less than or equal to the maximum value of the width of the protruding portions in the bent region. This is because when the width of the substrate in the end portion of the bent region is more than the maximum value of the width of the protruding portions in the bent region, variations in the width of a region in which no recessed portion is formed increase. The way how to cut out the substrate is not particularly limited, and a method for bending the substrate is not particularly limited. However, specific examples will be explained below as examples.

There is also another producing method including a step of cutting off at least an end portion of a substrate on which a plurality of recessed portions are arranged, a step of bending the substrate whose end portion has been cut off, in an arrangement direction in which the plurality of recessed portions are arranged, and a step of arranging metal in each of the recessed portions. This producing method is different from the above producing method in that the end portion of the substrate is cut off in a state in which metal is not arranged in the plurality of recessed portions formed on the substrate and that the step of arranging metal in each of the recessed portions is performed after the cutting step. However, the other points are the same, and therefore explanation for those same points will be omitted. Although a method for arranging metal in each of the recessed portions is not particularly limited, for example, plating, sputtering, vapor deposition, chemical vapor deposition (CVD), or the like may be used. In the case where metal is arranged in recessed portions with a high aspect ratio and a small pitch (20 micrometers or less) as in the X-ray shield grating for a Talbot interferometer, electroplating, by which metal can be relatively easily arranged in the recessed portions with high accuracy, is preferably used.

Examples of a cross section obtained when an X-ray shield grating according to an embodiment is cut in the direction in which a plurality of recessed portions are arranged are illustrated in FIGS. 1A to 1G.

The X-ray shield grating 1 of FIG. 1A includes the substrate 2 in which the width and the pitch of the plurality of recessed portions are constant and the pitch of the recessed portions is twice the width of the recessed portions. Therefore, throughout the substrate, the width of the protruding portions 6 is equal to the width of the recessed portions. The metal 4 is arranged in each of the recessed portions. FIG. 2 is a perspective view of the X-ray shield grating 1 of FIG. 1A. The X-ray shield grating 1 of FIG. 1A may be used as an X-ray shield grating in which each of the plurality of recessed portions has a line shape and the transmission portions and the shielding portions are arranged with the same width in one direction. In the X-ray shield grating 1 of FIG. 1A, the bent region 5 is bent in a cylindrical surface shape, and a region up to end faces of the substrate serves as a bent region. Left and right end portions 7a of the bent region are part of the substrate, and the width Wa of the substrate in the end portions is equal to the width of the protruding portions. As described above, the width of the substrate in the end portions is equal to the width of the protruding portions. Therefore, bending stress generated by bending the substrate 2 is distributed between each of the recessed portions and each of the protruding portions throughout the substrate 2. Accordingly, the X-ray shield grating 1 of FIG. 1A has a structure which is less likely to cause breakage of the substrate 2. In an X-ray shield grating of FIG. 1A, the width of the protruding portions in the bent region is constant, and therefore, the width of the substrate in the end portions of the bent region is equal to the minimum value of the width of the protruding portions in the bent region, and at the same time, equal to the maximum value of the protruding portions in the bent region. That is, the width of the substrate in the end portions of the bent region is less than or equal to the maximum value of the width of the protruding portions in the bent region.

Figure 1B:
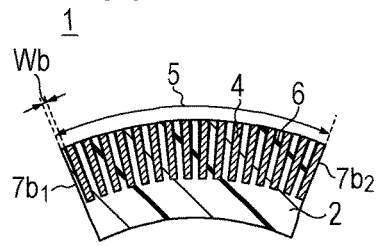

The X-ray shield grating 1 of FIG. 1B is different from the shield grating of FIG. 1A in that the width of the substrate differs between left and right end portions. However, the other points are the same as those in FIG. 1A, and therefore a detailed explanation for those same points will be omitted. In the X-ray shield grating 1 of FIG. 1B, an end portion $7b_1$ on the left side of the bent region 5 does not include metal, and width Wb of the substrate in the end portion is a half of the width of the protruding portions. In contrast, an end face $7b_2$ of the substrate on the right side of the bent region 5 includes metal, and the width of the substrate in the end portion is 0. Also in the substrate 2 of the X-ray shield grating of FIG. 1B, bending stress generated by bending the substrate 2 is distributed between each of the recessed portions and each of the protruding portions throughout the substrate 2. Accordingly, the X-ray shield grating 1 of FIG. 1B also has a structure which is less likely to cause breakage of the substrate 2.

Figure 1C:
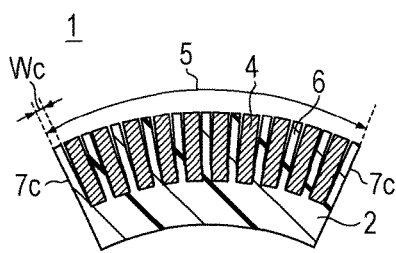

The X-ray shield grating 1 of FIG. 1C is different from the shield grating of FIG. 1A in that the pitch of the recessed portions is less than or equal to twice the width of the recessed portions and the width of the recessed portions is greater than the width of the protruding portions. However, the other points are the same as those in FIG. 1A, and therefore a detailed explanation for those same points will be omitted. Left and right end portions 7c of the bent region of the X-ray shield grating 1 of FIG. 1C are part of the substrate, and the width We of the substrate in the end portions is equal to the width of the protruding portions. As described above, even though the width of the recessed portions is greater than the width of the protruding portions, width of the protruding portions in the bent region is constant, and the width of the substrate in the end portions is equal to the width of the protruding portions in the bent region. Therefore, bending stress generated by bending the substrate 2 is distributed between each of the recessed portions and each of the protruding portions throughout the substrate 2. Accordingly, the X-ray shield grating 1 of FIG. 1C also has a structure which is less likely to cause breakage of the substrate 2.

Figure 1D:
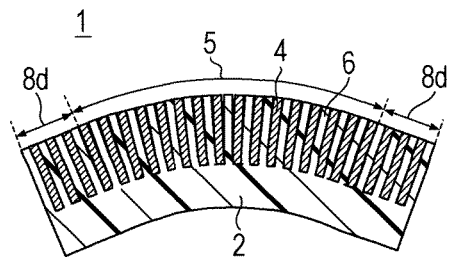

The X-ray shield grating 1 of FIG. 1D is different from the shield grating of FIG. 1A in that outer frame regions 8d which are in contact with the bent region are provided outside the bent region 5 and that the width of the end portions in the bent region is 0. However, the other points are the same as those in FIG. 1A, and therefore a detailed explanation for those same points will be omitted. The outer frame regions 8d also include a plurality of recessed portions in a manner similar to the bent region and the metal 4 is filled in each of the recessed portions. However, the outer frame regions 8d are different from the bent region 5 in that the radius of curvature at the cross section in the direction in which the recessed portions are arranged is more than 200 millimeters. As described above, even though the outer frame regions are provided, the width of the protruding portions in the bent region is constant and the width of the substrate in the end portions is equal to the width of the protruding portions in the bent region. Therefore, bending stress generated by bending the substrate 2 is distributed between each of the recessed portions and each of the protruding portions throughout the substrate 5. Accordingly, the X-ray shield grating 1 of FIG. 1D also has a structure which is less likely to cause breakage of the substrate 2.

Figure 1E:
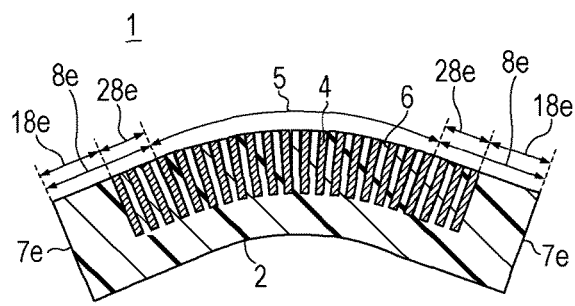

The X-ray shield grating 1 of FIG. 1E is different from the X-ray shield grating of FIG. 1D in that outer frame regions 8e include regions 18e where no recessed portion is formed, as well as regions 28e where a plurality of recessed portions are formed. However, the other points are the same as those in FIG. 1D, and therefore a detailed explanation for those same points will be omitted. The end portions of the X-ray shield grating are part of the substrate. The width of the substrate in the end portions of the X-ray shield grating (that is, the width of the regions 18e where no recessed portion is formed) is equal to or more than three times the minimum value of the width of the protruding portions in the bent region. However, in the regions where no recessed portion is formed, the radius of curvature is more than 200 millimeters. Bending stress is easily concentrated on a portion between a region where no recessed portion is formed and a recessed portion which is in contact with the region. In particular, if the width of the region where no recessed portion is formed is large, bending stress is easily concentrated on a portion between the region where no recessed portion is formed and a recessed portion which is in contact with the region. However, when the width of the protruding portions is constant in the bent region and the width of the substrate in the end portions of the bent region is 0, as with the X-ray shield grating 1 of FIG. 1E, even if a portion on which bending stress is easily concentrated exists within the outer frame regions 8e, the substrate is less susceptible to breakage. This is because the radius of curvature in the outer frame region is large (including infinity) and the generated bending stress itself is therefore small. The bending stress generated by bending the bent region is distributed between each of the recessed portions and each of the protruding portions throughout the substrate 5. Accordingly, the X-ray shield grating 1 of FIG. 1E also has a structure which is less likely to cause breakage of the substrate 2. As described above, in the outer frame regions in this embodiment, neither the width of the protruding portions nor the width of the substrate in the end portions is particularly limited. However, the end portions in the outer frame regions represent end portions of the substrate.

Figure 1F:
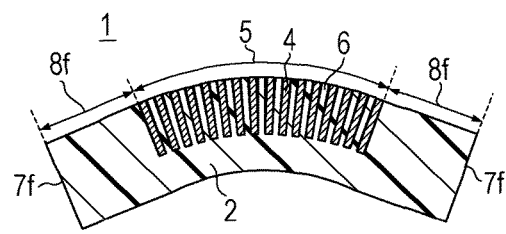

The X-ray shield grating 1 of FIG. 1F is different from the X-ray shield grating of FIG. 1D in that no recessed portion is formed in outer frame regions 8f. However, the other points are the same as those in FIG. 1D, and therefore a detailed explanation for those same points will be omitted. Accordingly, as with the shield grating of FIG. 1E, the X-ray shield grating 1 of FIG. 1F also has a structure which is less likely to cause breakage of the substrate 2.

Figure 1G:
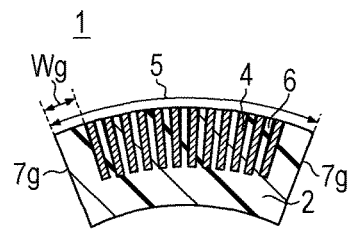

The X-ray shield grating 1 of FIG. 1G is different from the X-ray shield grating of FIG. 1A in that the width Wg of the substrate in the end portions of the bent region is three times the width of the protruding portions in the bent region. However, the other points are the same as those in FIG. 1A, and therefore a detailed explanation for those same points will be omitted. Since the width of the substrate in the end portions of the bent region is three times the width of the protruding portions in the bent region, bending stress is slightly more easily concentrated on a portion between a region sandwiched between an end portion of the bent region and the recessed portion closest to the end portion and the recessed portion which is in contact with the region than a portion between a protruding portion and a recessed portion which is in contact with the protruding portion. However, since the width of the substrate in the end portions of the bent region is less than or equal to three times the width of the protruding portions in the bent region, concentration of the bending stress can be reduced, and the substrate 2 is therefore less susceptible to breakage. Accordingly, the X-ray shield grating 1 of FIG. 1G also has a structure which is less likely to cause breakage of the substrate 2. However, in the bent region, the substrate is less likely to be broken when variations in the width of the protruding portions is smaller and the difference between the width of the substrate in the end portions and the minimum value of the width of the protruding portions is smaller. Therefore, the maximum value of the protruding portions and the width of the substrate in the end portions are preferably less than or equal to twice the minimum value of the protruding portions, and more preferably, less than or equal to one and a half times the minimum value of the protruding portions. In particular, in the bent region in which the radius of curvature is 100 millimeters or less, the maximum value of the protruding portions and the width of the substrate in the end portions are preferably less than or equal to twice the minimum value of the protruding portions, and more preferably, less than or equal to one and a half times the minimum value of the protruding portions.

A structural body produced by arranging metal in each of recessed portions arranged in one direction on the substrate may be used as a one-dimensional X-ray shield grating in which X-ray shielding portions and X-ray transmission portions are arranged one-dimensionally. Furthermore, the height direction of the metal 4 arranged in each of the recessed portions may be set toward the normal direction relative to a cylindrical surface. With this arrangement, the traveling direction of X rays and the height direction of the metal 4 may be made the same, and the X-ray shield grating may be used as an X-ray shield grating with a high transmission contrast of X rays. Furthermore, with the X-ray shield grating 1 according to this embodiment, unlike Japanese Patent Laid-Open No. 2012-13530, even if the substrate 2 is not reinforced using a bonding substrate, an X-ray shield grating which includes a bent region can be produced. Accordingly, an X-ray shield grating with a higher transmission contrast of X rays can be used. Even in the case where a bonding substrate is used, according to this embodiment, a thinner bonding substrate may be used. Therefore, compared to the case where this embodiment is not used, an X-ray shield grating with a higher transmission contrast of X rays can be produced.

In the X-ray shield grating according to this embodiment, X-ray transmission portions and X-ray shielding portions can be arranged with small pitches. Therefore, the X-ray shield grating can be used, in particular, as a source grating or an analysis grating in an X-ray Talbot interferometer. Above all, since the source grating requires a shorter distance to an X-ray source than the analysis grating and the source grating is required to be bent to have a smaller radius of curvature, it is highly effective to use the X-ray shield grating according to this embodiment.

Hereinafter, the present invention will be described in more detail by way of specific examples.

Example 1

In Example 1, a more specific example of the X-ray shield grating 1 illustrated in FIG. 1A will be explained. In Example 1, a silicon substrate is used as a substrate, and gold is used as metal. A method for producing the X-ray shield grating 1 according to Example 1 will be explained with reference to FIGS. 4A to 4E and FIGS. 5A and 5B.

First, a substrate on which a plurality of recessed portions are arranged and metal is arranged in each of the recessed portions is prepared. Such a substrate may be obtained by performing steps, for example, illustrated in FIGS. 4A to 4D. The steps illustrated in FIGS. 4A to 4D will be explained below.

Figure 4A:
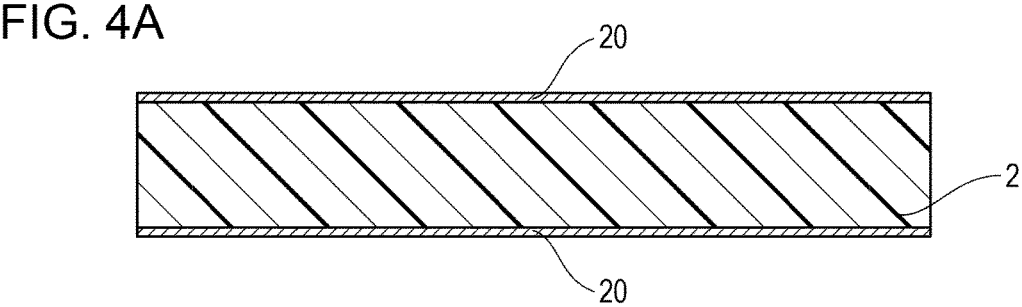
FIGS. 4A to 4E are diagrams for explaining a method for producing an X-ray shield grating according to Example 1 discussed herein.

A silicon substrate with a diameter of 100 millimeters, a thickness of 200 micrometers, and a resistivity of 0.02 Ωcm is used as the substrate 2. By thermally oxidizing the silicon substrate at 1,050 degrees Centigrade for 75 minutes, thermal oxide films 20 of about 0.5 micrometers are formed on front and rear surfaces of the silicon substrate (FIG. 4A).

Figure 4B:
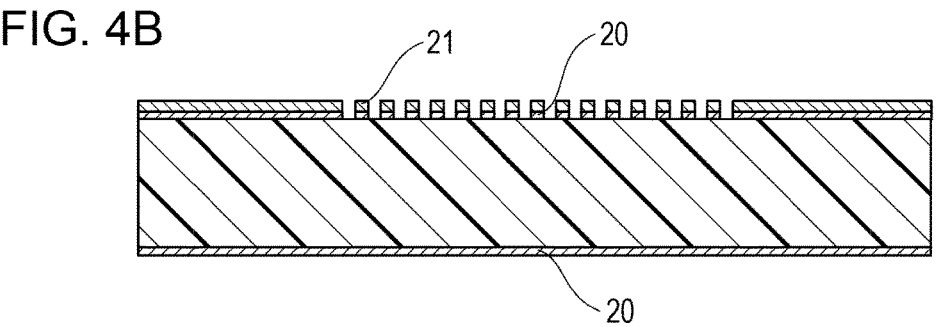

A chromium film of 200 nanometers is formed on one face by an electron beam vapor deposition device. A positive-type resist is applied onto the chromium film, and patterning is performed by semiconductor photolithography in such a manner that line-shaped resist opening patterns with a width of 6 micrometers are arranged in a stripe shape in a region of 55 millimeters×25 millimeters at a pitch of 12 micrometers. After that, the chromium is etched with a chromium etching solution, and then the thermal oxide film is etched with reactive etching using $CHF_3$. Accordingly, a pattern in which chromium line-shaped patterns of 6 micrometers are arranged in a stripe shape with a pitch of 12 micrometers on the silicon exposed face of 55 millimeters×25 millimeters, is formed (FIG. 4B). In Example 1, chromium masks 21, which are formed as described above, are used as etching masks.

Figure 4C:
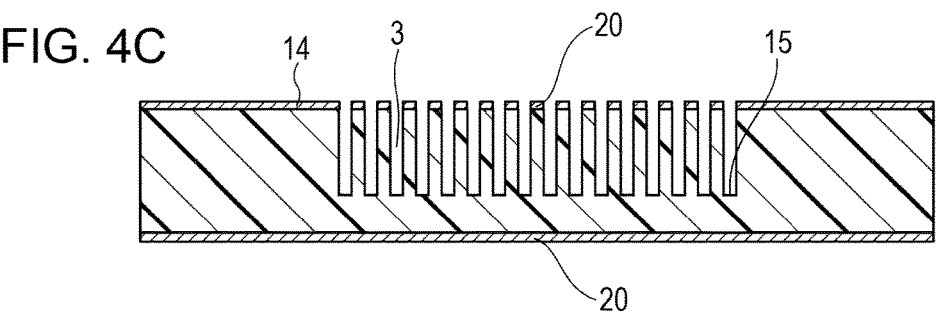

After that, anisotropic deep etching from a region in which silicon is exposed is performed using ICP-RIE, and recessed portions 3 are thus formed. When deep etching up to about 120 micrometers is performed, the deep etching is stopped. Accordingly, the plurality of recessed portions 3 with a depth of about 120 micrometers are formed in the silicon substrate (FIG. 4C).

Then, the resist and chromium are removed by UV-ozone asking and a chromium etching solution. After cleaning in a liquid mixture of sulfuric acid and hydrogen peroxide water and rinsing in water, the silicon substrate is dried.

By thermally oxidizing the silicon substrate at 1,050 degrees Centigrade for 7 minutes, a thermal oxide film of about 0.1 micrometers is formed on the surface of the silicon substrate on which the recessed portions 3 are formed by the above-described deep etching. Thus, thermal oxide films are also formed on the bottom faces and side walls of the recessed portions 3 (not illustrated).

Next, the thermal oxide films formed on bottom faces 15 of the recessed portions 3 are etched using a dry etching method by $CHF_3$ plasma. This etching has a high anisotropy and proceeds in a direction substantially perpendicular to the substrate. Therefore, the thermal oxide films on the bottom faces 15 of the recessed portions may be removed while the thermal oxide films on the side walls of the recessed portion are left.

Next, the electron beam vapor deposition device forms a chromium film of about 7.5 nanometers and a copper film of about 50 nanometers in that order to provide a seed electrode layer constituted of chromium and copper films to a silicon exposed surface. Since electron beam vapor deposition is a vapor deposition method with a high directionality, chromium and copper films are formed on the bottom faces 15 of the recessed portions and top faces 14 of the recessed portions.

Figure 4D:
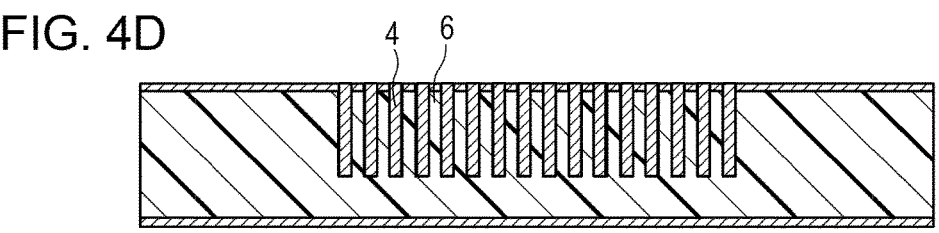

Next, part of the thermal oxide films around the silicon substrate is removed to expose the silicon surface, the exposed silicon surface is defined as a lead electrode for plating, and gold is arranged in the recessed portions 3 by electroplating using the lead electrode as a mold. Microfab Au1101 by Electroplating Engineers of Japan Ltd. is used as a gold plating solution to form a gold plating layer. When electrical connection is maintained for 26 hours while immersing the mold in the gold plating solution and setting the lead electrode as a negative pole at 60 degrees C. with a current density of 0.2 $A/dm^2$, a gold plating layer is formed until the gold plating layer flows out of the recessed portions. The overflown gold plating layer is removed by chemical mechanical polishing (CMP) (FIG. 4D). The above steps may be omitted by purchasing a substrate on which a plurality of recessed portions are arranged and metal is arranged in each of the recessed portions.

Figure 4E:
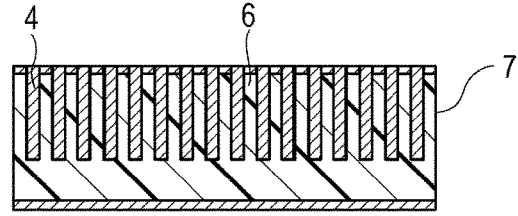

Next, a step of cutting off end portions of the substrate 2 is performed. In Example 1, a region including end portions of the substrate 2 is cut off in such a manner that the shortest distance from an end face of the substrate to a recessed portion (corresponding to the width Wa of the substrate in an end portion of a bent region) is 6 micrometers, and the substrate 2 with a size of 55 millimeters×25 millimeters is thus obtained (FIG. 4E).

Figure 5A:
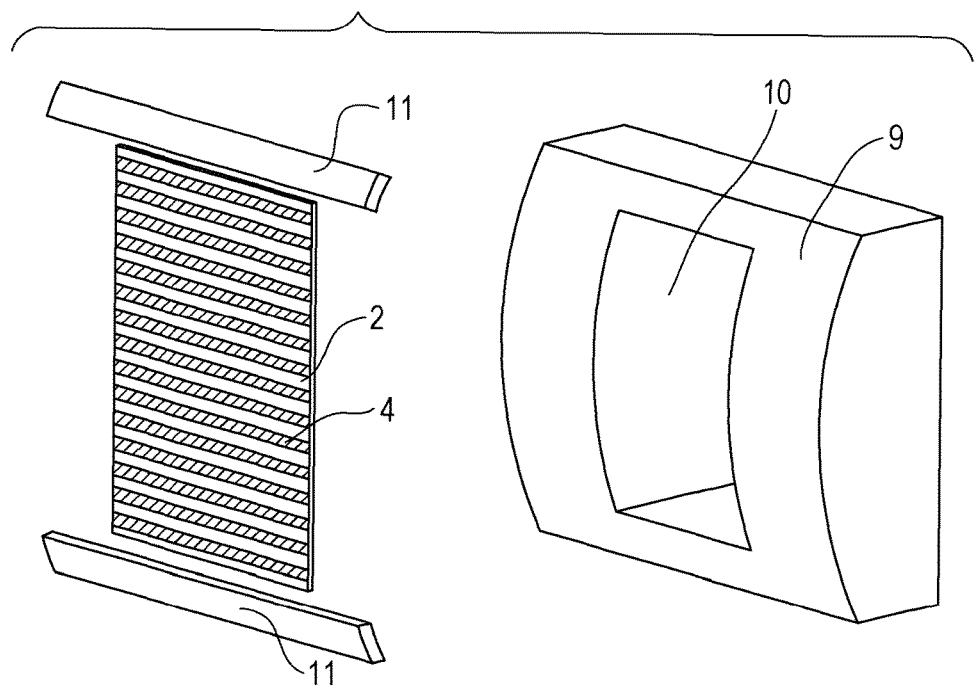
FIGS. 5A to 5B are diagrams for explaining a method for producing an X-ray shield grating according to Example 1 discussed herein.
Figure 5B:
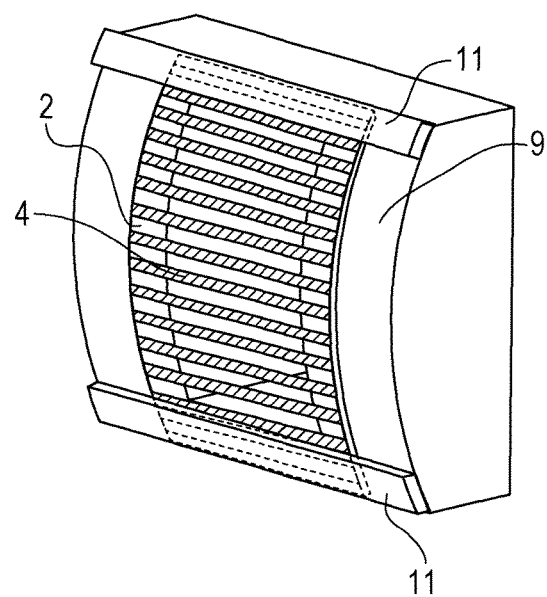

Next, a step of bending the substrate whose end portions have been cut off, in the direction in which the plurality of recessed portions are arranged, is performed. The substrate whose end portions have been cut off is bent using a supporting member 9 having a cylindrical surface with a radius of curvature of 149.8 millimeters, which is illustrated in FIG. 5A. A through hole 10 of 50 millimeters×20 millimeters is provided at the supporting member 9. The substrate 2 whose end portions have been cut off is bent in the direction in which the plurality of recessed portions are arranged, and the substrate 2 is pressed against the cylindrical surface of the supporting member in such a manner that the shape of the substrate 2 whose end portions have been cut off follows the shape of the cylindrical surface of the supporting member 9. Then, the substrate 2 is fixed at the supporting member 9 with fixing devices 11 (FIG. 5B). Accordingly, the X-ray shield grating 1 of 55 millimeters×25 millimeters which is bent so as to have a cylindrical surface is obtained. By defining the face of the substrate 2 that is pressed against the cylindrical surface of the supporting member 9 (the face in contact with the cylindrical surface) as a face which opposes the face on which the plurality of recessed portions are formed, the substrate 2 easily follows the shape of the cylindrical surface. Furthermore, by using a silicon substrate in which the face which opposes the face on which the plurality of recessed portions are formed is a mirror face, the substrate 2 follows the shape of the cylindrical surface of the supporting member 9 more easily. This is because the smoother the face which is pressed against the cylindrical surface of the supporting member 9 of the silicon substrate, the more easily the substrate 2 follows the shape of the cylindrical surface.

Regarding the shape of the face of the X-ray shield grating 1 that opposes the face which is in contact with the supporting member (a paper surface side of FIG. 5B), the radius of curvature is 150 millimeters. Furthermore, by using a region exposed through the through hole 10 of 50 millimeters×20 millimeters of the supporting member 9 as a grating region of the X-ray shield grating, the X-ray shield grating may be used as an X-ray shield grating including a grating region with a high transmission contrast. Instead of providing a through hole, a supporting member may be formed using a material with a high X-ray transmission rate. However, providing a through hole as in Example 1 is preferable because a high transmission contrast can be achieved.

Example 2

In Example 2, a specific example in which a substrate thicker than that used in Example 1 is used and an X-ray shield grating is bent in a method different from Example 1 will be explained. However, the other points are same as those in Example 1, and therefore a detailed explanation for those same points will be omitted.

Processing up to the step of cutting off end portions is performed in a manner similar to Example 1 with the exception that a silicon substrate with a thickness of 300 micrometers is used as the substrate 2, and the substrate 2 of 55 millimeters×25 millimeters on which a plurality of recessed portions are arranged and gold is arranged in each of the recessed portions is obtained.

Figure 6A:
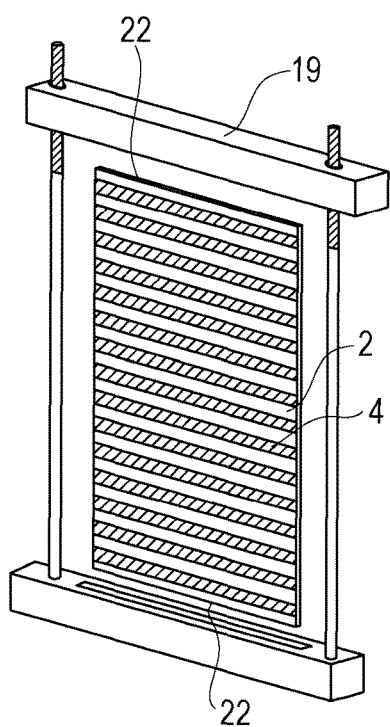
FIGS. 6A to 6B are diagrams for explaining a method for producing an X-ray shield grating according to Example 2 discussed herein.
Figure 6B:
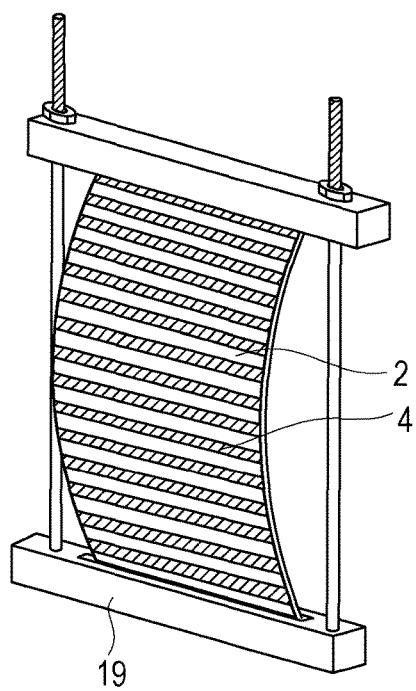

In Example 2, a step of bending the substrate whose end portions have been cut off, in the direction in which the plurality of recessed portions are arranged, is performed using supporting members 19 illustrated in FIGS. 6A and 6B. The supporting members 19 used in Example 2 are used for bending the substrate 2 in a cylindrical surface shape by applying loads onto side faces 22 of the substrate in parallel. When loads are applied to the supporting members 19 from a face vertical to the direction in which the plurality of recessed portions are arranged, the substrate 2 is bent in the direction in which the plurality of recessed portions are arranged. Therefore, the substrate 2 is not broken even with a radius of curvature of 200 millimeters. By stopping further application of loads from the supporting member at the time when the radius of curvature of the substrate reaches 200 millimeters, the X-ray shield grating 1 with a radius of curvature of 200 millimeters is obtained.

Comparative Example

In this comparative example, an X-ray shield grating is produced in a manner similar to the method for producing an X-ray shield grating according to Example 2 with the exception that end portions of the substrate is cut off in such a manner that the shortest distance from an end face of the substrate to a recessed portion is 20 micrometers in the step of cutting off end portions.

Figure 10A:
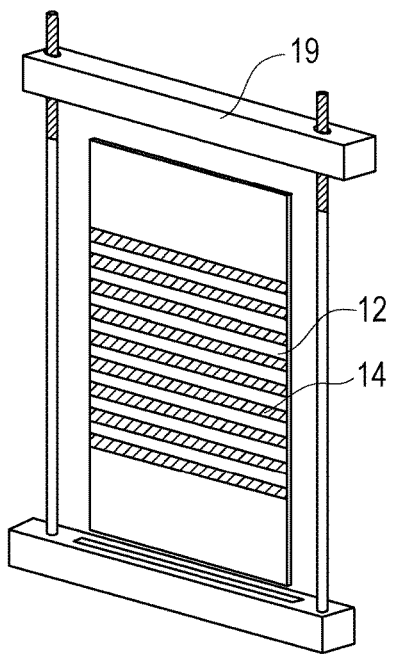
FIGS. 10A to 10B are diagrams according to Comparative Example 1 discussed herein.
Figure 10B:
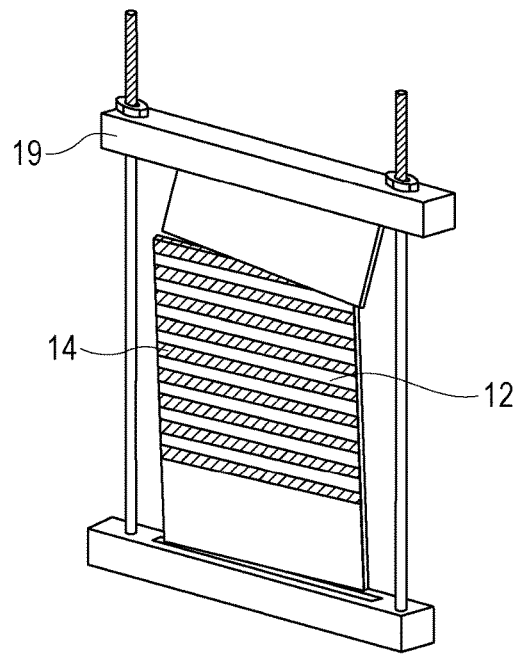

As illustrated in FIGS. 10A and 10B, when loads are applied to the substrate 12 using the supporting members 19 as in Example 2 so that the substrate 12 is bent in the direction in which the plurality of recessed portions are arranged (corresponding to the direction in which the metal 14 is arranged), the substrate 12 becomes broken before the radius of curvature is changed into 200 millimeters.

Example 3

In Example 3, a specific example of the X-ray shield grating 1 illustrated in FIG. 1F will be explained. Example 3 is different from Example 1 in that the end portions of the substrate are cut off in such a manner that the width of the substrate in the end portions of the substrate is 10 millimeters in the step of cutting off the end portions of the substrate and that the substrate is bent in such a manner that not the entire substrate but only part of the substrate serves as a bent region. The other points are the same as those in Example 1, and a detailed explanation for those same points will be omitted.

In Example 3, a step of cutting off end portions of the substrate 2 is performed. In Example 3, end portions of the substrate are cut off in such a manner that the shortest distance from an end face of the substrate to metal is 10 millimeters, and the substrate 2 of 75 millimeters x 25 millimeters is thus obtained.

As illustrated in FIG. 7, by using the supporting member 9 and the fixing devices 11 similar to those in Example 1, the substrate is pressed against the supporting member, and the substrate 2 is fixed at the supporting member with the fixing devices 11, so that the region of 55 millimeters×25 millimeters in which the recessed portions and the protruding portions are formed follows the cylindrical surface of the supporting member 9. Accordingly, the region of 55 millimeters×25 millimeters in which gold is filled in the recessed portions 3 has a bent shape which includes a cylindrical surface with a radius of curvature of 150.0 millimeters. Thus, the X-ray shield grating 1 with a radius of curvature of 150.0 millimeters is obtained. Here, a region of the substrate that is 10 millimeters away from an end portion on the side of the arrangement direction of the substrate (face vertical to the arrangement direction of the substrate) is not in contact with the cylindrical surface of the supporting member 9. Therefore, the radius of curvature of the region is more than 200 millimeters. Therefore, the bending stress itself generated in this region can be reduced, and the substrate is not broken. Instead of using a supporting member which is smaller than the substrate whose end portions have been cut off as described above, a supporting member which includes a cylindrical surface with a region of 55 millimeters×25 millimeters with a radius of curvature of 149.8 millimeters and a cylindrical surface of a radius of curvature greater than 198.8 millimeters outside the region may be used. With the use of such a supporting member, the radius of curvature of a region which is 10 millimeters away from an end portion on the side of the arrangement direction of the substrate can be reliably made greater than 200 millimeters.

Example 4

In Example 4, an X-ray Talbot-Lau interferometer 1000 which uses the X-ray shield grating 1 according to Example 1 as a source grating will be explained with reference to FIG. 8.

The X-ray Talbot-Lau interferometer 1000 according to Example 4 is an interferometer using an X-ray Talbot-Lau interference method. The X-ray Talbot-Lau interferometer 1000 includes an X-ray source 100 which emits divergent X rays, a diffraction grating 200 which diffracts X rays, an analysis grating 300 in which X-rays shielding portions and X-ray transmission portions are arranged, and a detector 500 which detects X rays from the analysis grating. Furthermore, the X-ray Talbot-Lau interferometer 1000 includes the shield grating according to Example 1 as a source grating 400. When the source grating 400 is arranged between the X-ray source 100 and the diffraction grating 200, a state in which X rays from the X-ray source are divided and microfocus X-ray sources are virtually arranged can be generated. The X rays emitted from the microfocus X-ray sources are applied to the diffraction grating.

In order to reduce vignetting of X rays caused by the source grating, it is preferable that the source grating and the X-ray source are arranged so that the center of curvature of a grating region of the source grating and the focal point of the X-ray source match.

The diffraction grating 200 forms an interference pattern by diffracting X rays from the source grating 400, and the analysis grating 300 forms moire by shielding part of the X rays forming the interference pattern. The diffraction grating 200 and the analysis grating 300 each have a one-dimensional periodic structure. That is, the diffraction grating 200 is a one-dimensional diffraction grating which forms a one-dimensional interference pattern, and the analysis grating is a one-dimensional analysis grating (one-dimensional shield grating) in which the X-ray transmission portions and the X-ray shielding portions are periodically arranged in one direction. By arranging a subject 600 between the source grating 400 and the diffraction grating 200, an interference pattern is changed by the influence of the subject, and the moire formed by the interference pattern and the analysis grating 300 is also changed. The detector 500 detects the intensity of X rays which form the moire, and information of the subject is obtained from the result of the detection. In the case where an interference pattern can be directly detected by the detector, the analysis grating may not be used. Furthermore, although the subject 600 is arranged between the source grating and the diffraction grating in FIG. 8, the subject 600 may be arranged between the diffraction grating and the analysis grating (if an analysis grating is not used, the detector). Furthermore, in the case where X rays emitted from the X-ray source 100 are diffracted by the diffraction grating and thus have an enough coherency to form an interference pattern, the source grating 400 may not be used. The X-ray shield grating according to this embodiment may be used as an analysis grating, irrespective of whether the X-ray Talbot interferometer which does not use a source grating is used or the X-ray Talbot-Lau interferometer which uses a source grating is used.

Figure 8:
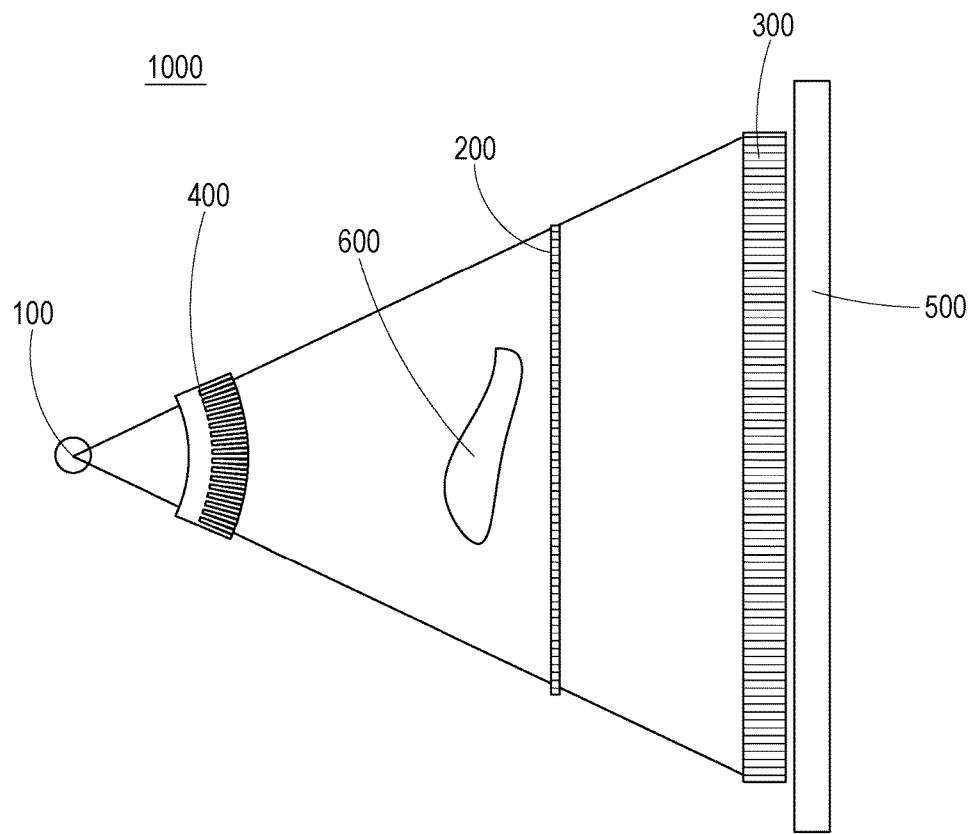
FIG. 8 is a schematic diagram of a Talbot-Lau interferometer according to Example 4 discussed herein.

Furthermore, although the Talbot-Lau interferometer of FIG. 8 includes an X-ray source, the X-ray shield grating according to the above embodiment may be used as a source grating or an analysis grating of a Talbot interferometer not including an X-ray source. A Talbot interferometer not including an X-ray source may be combined with an X-ray source to perform measurement of a subject. Such a Talbot interferometer may be combined with an X-ray source owned by a user or may be combined with various X-ray sources according to measurement (for example, depending on energy emitted). Furthermore, the X-ray shield grating according to the above embodiment may be used as a source grating used for an X-ray irradiation unit for a Talbot-Lau interferometer including an X-ray source and a source grating. An X-ray irradiation unit for a Talbot-Lau interferometer may be combined with a Talbot interferometer which includes at least a diffraction grating and a detector to perform measurement of a subject.

Example 5

In Example 5, a specific example of an X-ray shield grating 201 illustrated in FIGS. 11A and 11B will be explained.

Figure 11A:
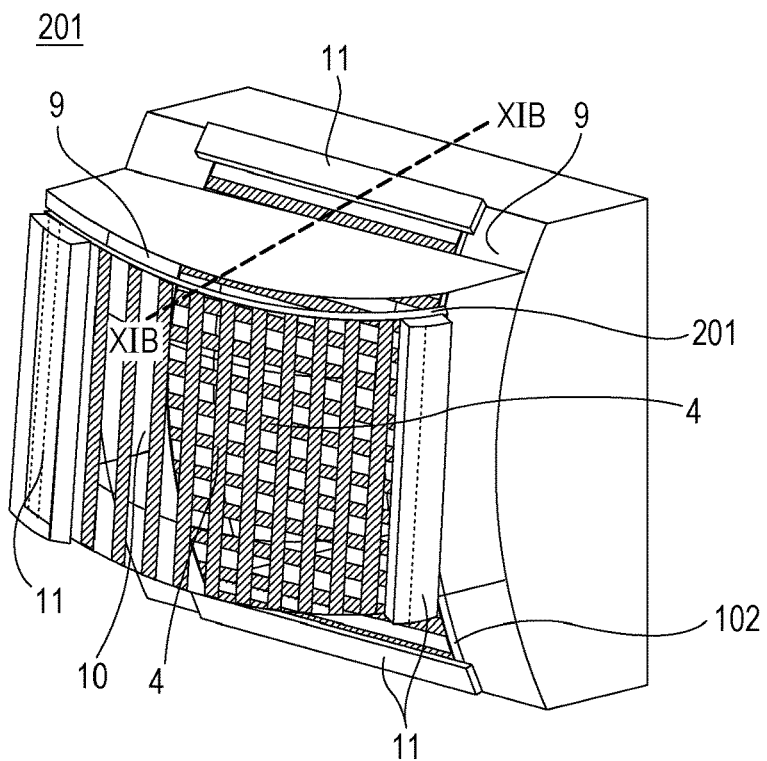
FIGS. 11A and 11B are diagrams of an X-ray shield grating according to Example 5 discussed herein.

FIG. 11A is a perspective view of the X-ray shield grating 201. Example 5 is different from Example 1 in that the X-ray shield grating 201 includes two substrates 2 (hereinafter, may be referred to as partial shield gratings) on which the metal 4 is arranged between the protruding portions 6 of FIG. 4E of Example 1 and has two periodic directions. However, the other points are similar to those in Example 1. A first partial shield grating 102 is bent using the supporting member 9 (a radius of curvature of 149.8 millimeters) that is the same as in Example 1, and a second partial shield grating 202 is bent using a supporting member (a radius of curvature of 159.8 millimeters), which is different from the supporting member 9 in Example 1 only in the radius of curvature. As in Example 1, since the substrates of the partial shield gratings 102 and 202 have a thickness of 200 micrometers, the radius of curvature of a face of the partial shield grating 102 that opposes the face that is in contact with the supporting member is 150 millimeters, and the radius of curvature of a face of the partial shield grating 202 that opposes the face that is in contact with the supporting member is 160 millimeters. Accordingly, the partial shield gratings 102 and 202 which are bent so that the radiuses of curvature of the partial shield gratings are different from each other can be obtained.

As illustrated in FIG. 11A, the two partial shield gratings 102 and 202 are arranged in such a manner that the periodic directions of the partial shield gratings intersect each other (orthogonal in FIGS. 11A and 11B) and the partial shield grating 102, which has a smaller radius of curvature, is located at the inner side of the bending.

Figure 11B:
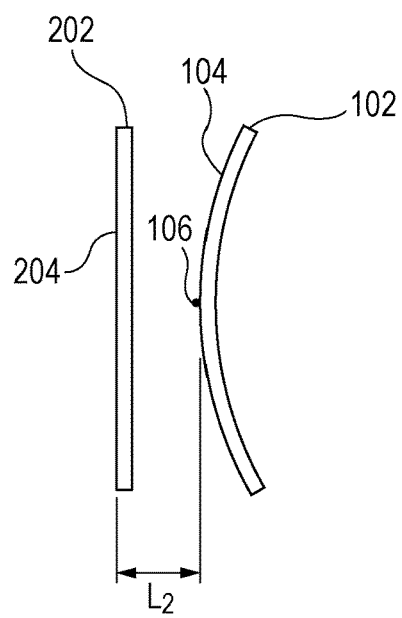

FIG. 11B is a schematic diagram illustrating a positional relationship between the two partial shield gratings 102 and 202 in the X-ray shield grating 201. FIG. 11B is a cross-sectional view taken along line XIB-XIB of FIG. 11A, and the cross section is parallel to the periodic direction of the partial shield grating 202. FIG. 11B is a schematic diagram for illustrating the positional relationship between the two partial shield gratings 102 and 202, and therefore, the supporting member 9 is not illustrated in FIG. 11B. In the X-ray shield grating 201, the distance $L_2$ between the two partial shield gratings 102 and 202 is 10 millimeters. The distance $L_2$ between the partial shield gratings represents the distance between center lines in the periodic direction of the partial shield gratings. The center line in the periodic direction of the partial shield grating 102 indicates a center line 106 in the periodic direction of the partial shield grating 102 on a face 104 of the partial shield grating 102 that opposes the face that is in contact with the supporting member. Similarly, the center line in the periodic direction of the partial shield grating 202 indicates a center line in the periodic direction of the partial shield grating 202 on a face 204 of the partial shield grating 202 that opposes the face that is in contact with the supporting member. FIG. 11B is a cross-sectional view illustrating the cross section which is parallel to the periodic direction of the substrate 202, and therefore, the center line in the periodic direction on the face 204 of the substrate 202 corresponds to the face 204 in FIG. 11B.

The two partial shield gratings are arranged in such a manner that the periodic directions correspond to each other, the partial shield grating 102, which has a smaller radius of curvature, is located at the inner side of the bending, and the distance $L_2$ between the partial shield gratings is 10 millimeters, and then the partial shield grating 202 is arranged at a position rotated by 90 degrees. Accordingly, the periods of the metal 4 formed in a line shape in the two partial shield gratings 102 and 202 orthogonally intersect each other, and the X-ray transmission portions (a region where the transmission portions (protruding portions) of the partial shield gratings are stacked) are arranged in a substantially two-dimensional manner. Since the through holes of the supporting members 9 are also stacked, by using a region of 20 millimeters×20 millimeters where the through holes overlap as a grating region of the X-ray shield grating, the X-ray shield grating may be used as an X-ray shield grating in which the X-ray transmission portions are arranged two-dimensionally and which includes a grating region with a high transmission contrast. In addition, the distance $L_2$ between the two partial shield gratings and the difference in the radiuses of curvature of the two partial shield gratings (160 millimeters−150 millimeters=10 millimeters) are the same. Accordingly, lines connecting the centers of curvature of the two partial shield gratings intersect each other. A line connecting the center of curvature of a partial shield grating corresponds to the rotation central axis when a cylinder whose side face (curved face) is formed by the partial shield grating is defined as a rotating body. By arranging the focal point of an X-ray source at a point where the centers of curvature intersect each other, the focal point of the X-ray source may be arranged at the center of curvature of the two partial shield gratings. Accordingly, vignetting of X rays caused by the X-ray shield grating can be reduced compared to the case where the distance $L_2$ between the two partial shield gratings and the difference in the radiuses of curvature of the two partial shield gratings are not the same.

Example 6

In Example 6, an X-ray Talbot-Lau interferometer which uses the X-ray shield grating 201 according to Example 5 as a source grating will be explained. Example 6 is different from Example 4 in that a source grating in the X-ray Talbot-Lau interferometer is the X-ray shield grating 201 according to Example 5 and the diffraction grating and the analysis grating have a two-dimensional periodic structure. However, the other points are the same as those in Example 4, and a detailed explanation for those same points will be omitted.

The X-ray shield grating 201 according to Example 5 is arranged in such a manner that the centers of curvature of two substrates and the focal point of the X-ray source match. The X-ray shield grating may be arranged in such a manner that the distance between the substrate 102 of the X-ray shield grating, which has a smaller radius of curvature, and the focal point of the X-ray source is 150 millimeters and the X-ray source is arranged on the extension of the line segment connecting the center lines in the periodic direction of the two substrates 102 and 202.

When the X-ray shield grating 201 is arranged between the X-ray source and the diffraction grating, the X-ray shield grating 201 functions as a source grating, and generates a state in which X rays from the X-ray source are divided and microfocus X-ray sources are virtually arranged in two-dimensionally. Then, the X rays emitted from the microfocus X-ray sources are applied to the diffraction grating. The diffraction grating has a two-dimensional periodic structure, and X rays emitted from virtual microfocus X-ray sources form a two-dimensional interference pattern having periods in two directions. Furthermore, in the analysis grating, the X-ray shielding portions and the X-ray transmission portions are arranged two-dimensionally, and the X-ray detector detects the two-dimensional intensity distribution having periods in two directions.

The Talbot interferometer is a shearing interferometer, and is therefore able to acquire information of a wavefront differentiated based on a detection result. By detecting two-dimensional intensity distribution as in Example 6, information of a wavefront differentiated in two different directions based on a single detection result (so-called X-shear information and Y-shear information) can be obtained. That is, two differential phase images can be obtained from a single detection result.

Preferred embodiments of the present invention have been described above. However, the present invention is not limited to the foregoing embodiments and various changes and modifications may be made to the present invention without departing from the scope of the present invention.

Furthermore, the technical elements described herein or illustrated in the drawings exert technical utility separately or in combination, and are not limited to a combination of claims as originally filed. Moreover, the techniques described herein or illustrated by way of example in the drawings are intended to simultaneously achieve a plurality of purposes, and have technical utility by achieving one of the purposes.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-093889 filed Apr. 30, 2014 and No. 2015-005924 filed Jan. 15, 2015, which are hereby incorporated by reference herein in their entirety.

What is claimed is:

1. An X-ray shield grating comprising:
a substrate on which a plurality of recessed portions are arranged; and metal that is arranged in each of the recessed portions,
wherein the substrate includes a bent region that is bent in an arrangement direction in which the plurality of recessed portions are arranged,
wherein a radius of curvature of the bent region is 200 millimeters or less, and
wherein in the bent region,
in a case where a maximum value of a width of a region sandwiched between two adjacent recessed portions of the plurality of recessed portions is less than or equal to three times a minimum value of the width of the region sandwiched between the two adjacent recessed portions, and
in a case where a width of the substrate in an end portion of the bent region represents a shortest distance from the end portion to the metal when the end portion is part of the substrate, and represents 0 when the end portion is part of the metal,
wherein the end portion is cut off so the width of the substrate in the end portion of the bent region being less than or equal to three times the minimum value of the region sandwiched between the two adjacent recessed portions of the plurality of recessed portions,
wherein the substrate includes an outer frame region that is in contact with the bent region, and the radius of curvature of the outer frame region is greater than 200 millimeters, and
wherein the substrate has a first surface including the metal arranged in the plurality of the recessed portions and a second surface that is located on the opposite side of the first surface, and the first surface is broadened compared with the second surface.

2. An X-ray shield grating comprising:
a substrate on which a plurality of recessed portions are arranged; and
metal that is arranged in each of the recessed portions,
wherein the substrate includes a bent region that is bent in an arrangement direction in which the plurality of recessed portions are arranged,
wherein a radius of curvature of the bent region is 200 millimeters or less, and
wherein in the bent region,
in a case where a maximum value of a width of a region sandwiched between two adjacent recessed portions of the plurality of recessed portions is less than or equal to three times a minimum value of the width of the region sandwiched between the two adjacent recessed portions, and
in a case where a width of the substrate in an end portion of the bent region represents a shortest distance from the end portion to the metal when the end portion is part of the substrate, and represents 0 when the end portion is part of the metal, the width of the substrate in the end portion of the bent region being less than or equal to three times the minimum value, and
wherein the bent region is also bent in a direction perpendicular to the arrangement direction.

3. The X-ray shield grating according to claim 2, wherein the substrate is made of silicon or glass.

4. An X-ray Talbot interferometer comprising:
a source grating configured to divide divergent X rays from an X-ray source;
a diffraction grating configured to form an interference pattern by diffracting X rays from the source grating; and
a detector configured to detect X rays that form the interference pattern, wherein the source grating is the X-ray shield grating according to claim 2.

5. The X-ray Talbot interferometer according to claim 4, further comprising:
an analysis grating configured to shield part of the X rays that form the interference pattern,
wherein the detector detects the X rays that form the interference pattern by detecting X rays from the analysis grating.

6. An X-ray Talbot interferometer comprising:
a diffraction grating configured to form an interference pattern by diffracting divergent X rays from an X-ray source;
an analysis grating configured to shield part of X rays that form the interference pattern; and
a detector configured to detect X rays from the analysis grating,
wherein the analysis grating is the X-ray shield grating according to claim 2.

7. An X-ray irradiation unit for a Talbot-Lau interferometer, comprising:
an X-ray source; and
a source grating,
wherein the source grating is the X-ray shield grating according to claim 2.

8. A method for producing an X-ray shield grating, comprising:
a step of cutting off at least an end portion of a substrate on which a plurality of recessed portions are arranged and metal is arranged in each of the recessed portions; and
a step of bending the substrate whose end portion has been cut off, in an arrangement direction in which the plurality of recessed portions are arranged,
wherein in the bending step, the substrate whose end portion has been cut off is bent in such a manner that at least part of the substrate whose end portion has been cut off becomes a bent region with a radius of curvature of 200 millimeters or less, and
wherein in the bent region,
in a case where a maximum value of a width of a region sandwiched between two adjacent recessed portions of the plurality of recessed portions is less than or equal to three times a minimum value of the width of the region sandwiched between the two adjacent recessed portions, and
in a case where a width of the substrate in the end portion of the bent region represents a shortest distance from the end portion to the metal when the end portion is part of the substrate, and represents 0 when the end portion is part of the metal,
in the step of cutting off the end portion,
the end portion is cut off so the width of the substrate in the end portion of the bent region is less than or equal to three times the minimum value of the width of the region sandwiched between the two adjacent recessed portions of the plurality of recessed portions.

9. The method for producing an X-ray shield grating according to claim 8,
wherein in the step of cutting off the end portion,
the end portion is cut off so the width of the substrate in the end portion of the bent region is smaller than the maximum value of the width of the region sandwiched between the two adjacent recessed portions in the bent region.

* * * * *